United States Patent [19]

Nevin

[11] Patent Number: 5,753,890
[45] Date of Patent: May 19, 1998

[54] NON-FOGGING MIRROR FOR DENTAL OR MEDICAL USE

[76] Inventor: Donald Nevin, 3 Clearmeadow Ct., Woodbury, N.Y. 11797

[21] Appl. No.: 585,294

[22] Filed: Jan. 11, 1996

[51] Int. Cl.[6] .................. H05B 1/00; A61B 1/24; A61C 3/00
[52] U.S. Cl. .................. 219/219; 433/30; 433/32
[58] Field of Search .................. 219/219, 522, 219/541; 359/512, 513, 514; 433/30, 31, 32

[56] References Cited

U.S. PATENT DOCUMENTS

| 281,224 | 7/1883 | Goodsell et al. | 433/30 |
|---|---|---|---|
| 709,812 | 9/1902 | Bennett et al. | 433/30 |
| 1,934,110 | 11/1933 | Wilson | 433/30 |
| 3,513,290 | 5/1970 | Burley et al. | 219/227 |
| 4,568,281 | 2/1986 | Harvey et al. | 433/30 |
| 4,631,391 | 12/1986 | Tiepke | 219/219 |
| 4,993,945 | 2/1991 | Kimmelman et al. | 433/30 |
| 5,099,514 | 3/1992 | Acree | 379/441 |
| 5,558,428 | 9/1996 | Lehrer et al. | 362/105 |

*Primary Examiner*—Teresa J. Walberg
*Assistant Examiner*—Sam Paik
*Attorney, Agent, or Firm*—Robert L. Epstein; Harold James; James & Franklin

[57] ABSTRACT

A casing seals to the edge of a mirror blank to form an autoclavable unit. An electrically energizable heater element is enclosed within the unit. The element is connected to a plug which extends from the casing and is adapted to engage a socket when the unit nests in a recess in a rack. A transformer is connected to the socket such that the heater is energized to preheat the unit while in the rack. Removal of the unit from the rack disconnects the electric supply, permitting the preheated unit to used without danger of shock. Several units may be preheated simultaneously on a single rack.

21 Claims, 3 Drawing Sheets

FIG. 1

FIG. 3
FIG. 4
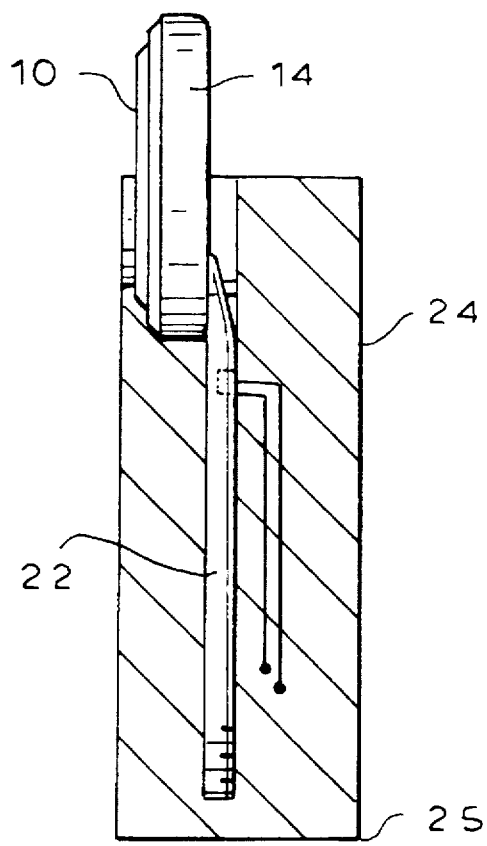
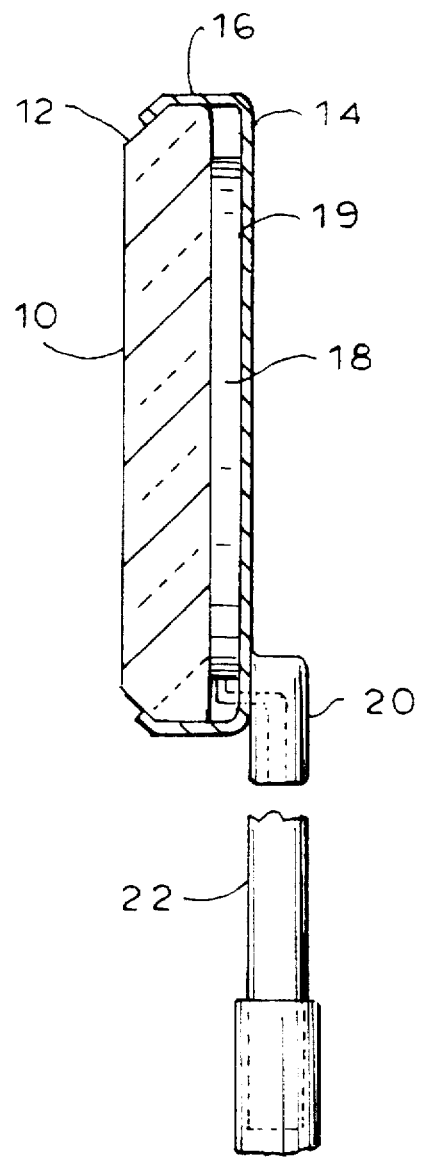

NON-FOGGING MIRROR FOR DENTAL OR MEDICAL USE

The present invention relates to hand held mirrors for dental and medical use and more particularly to a mirror which is preheated to prevent fogging but which presents no damage of electrical shock or burning the patient.

Hand held mirrors are commonly used for dental purposes and for certain medical applications, such as for laryngoscopic procedures. Such mirrors tend to fog when placed in the oral cavity because water vapor present in the oral cavity condenses on the mirror surface, which is generally cooler than the temperature of the oral cavity.

One common solution to prevent fogging in dental use is to coat the mirror surface prior to insertion into the oral cavity with a defogging solution, which is essentially a soap film. However, this introduces additional chemistry into the oral cavity. Moreover, the film may tend to obscure the image.

In laryngoscopy, the physician will normally heat the mirror in a flame to prevent fogging. However, this approach does not permit any real control over how hot the mirror becomes. Thus there is risk of burning the patient.

The present invention overcomes these problems by providing a completely sealed, autoclavable, hand-held mirror unit containing an electric heater which, when nested in a rack, is preheated to a preset temperature. The unit has a plug which disengages a socket in the rack when the unit is removed such that there is no danger of electric shock.

The rack may accomodate a plurality of mirror units simultaneously. The rack is associated with a DC transformer which can be unplugged from the rack so that the rack itself can be autoclaved.

It is, therefore, a prime object of the present invention to provide a non-fogging mirror for dental and medical purposes.

It is another object of the present invention to provide a non-fogging mirror which may be preheated to a controlled temperature level prior to use.

It is another object of the present invention to provide a non-fogging mirror which is autoclavable.

It is another object of the present invention to provide a rack for a plurality of preheatable mirrors.

In accordance with one aspect of the present invention, a non-fogging mirror is provided. The mirror consists of a mirror blank having an edge and a rear surface. A casing is sealed to the mirror edge. The casing defines a cavity adjacent the rear surface of the mirror. An electrically energizable heat generating means is situated within the cavity. Means are provided for operably electrically connecting the heat generating means to a source of electricity. The connecting means includes first and second interengaging parts. The first part is mounted on and sealed to the casing. The second part is operably connected to the electric source, so as to energize the heat generating means.

The first part may be a plug, preferably a two pronged plug. The second part may be a socket. A D.C. transformer is connected to the electric source. The transformer has an output. The second part is connected to the transformer output. Rack means are provided for supporting the mirror. The rack means includes the second part. The first and said second parts interengage when the mirror is supported by the rack means.

In accordance with another aspect of the present invention, an energization system for a mirror unit is provided. The system includes rack means for supporting the mirror unit. A source of electricity is provided. The unit includes a mirror, electrically energizable heat generated means and a casing sealed to the mirror defining a cavity within which the heat generating means is situated. First interengaging means are mounted on the casing. The rack means includes second interengaging means operably electrically connected to the source and associated with the supporting means, such that the first interengaging means of the unit interengages the second interengaging means when the unit is received in the supporting means so as to electrically connect the heat generating means with said source.

The interengaging means may be first a plug, preferrably a two pronged plug. The second interengaging means includes a socket.

A D.C. transformer is connected to the electric source. The transformer has an output. The socket is connected to the transformer output.

The rack means may include first and second supporting means for supporting first and second mirror units.

The second interengaging means may include first and second interengaging parts. Each of the parts is associated with a different one of the supporting means.

In accordance with the above, and to such other objects which may hereinafter appear, the present invention relates to a non-fogging mirror for dental or medical use as set forth in detail in the following specification and recited in the annexed claims, taken together with the accompanying drawings, wherein like numbers relate to like parts, and in which:

FIG. 3 is a side cross sectional view taken along line 3—3 of FIG. 1; and

FIG. 4 is an enlarged cross-sectional view of one of the mirror units.

Figure 1:
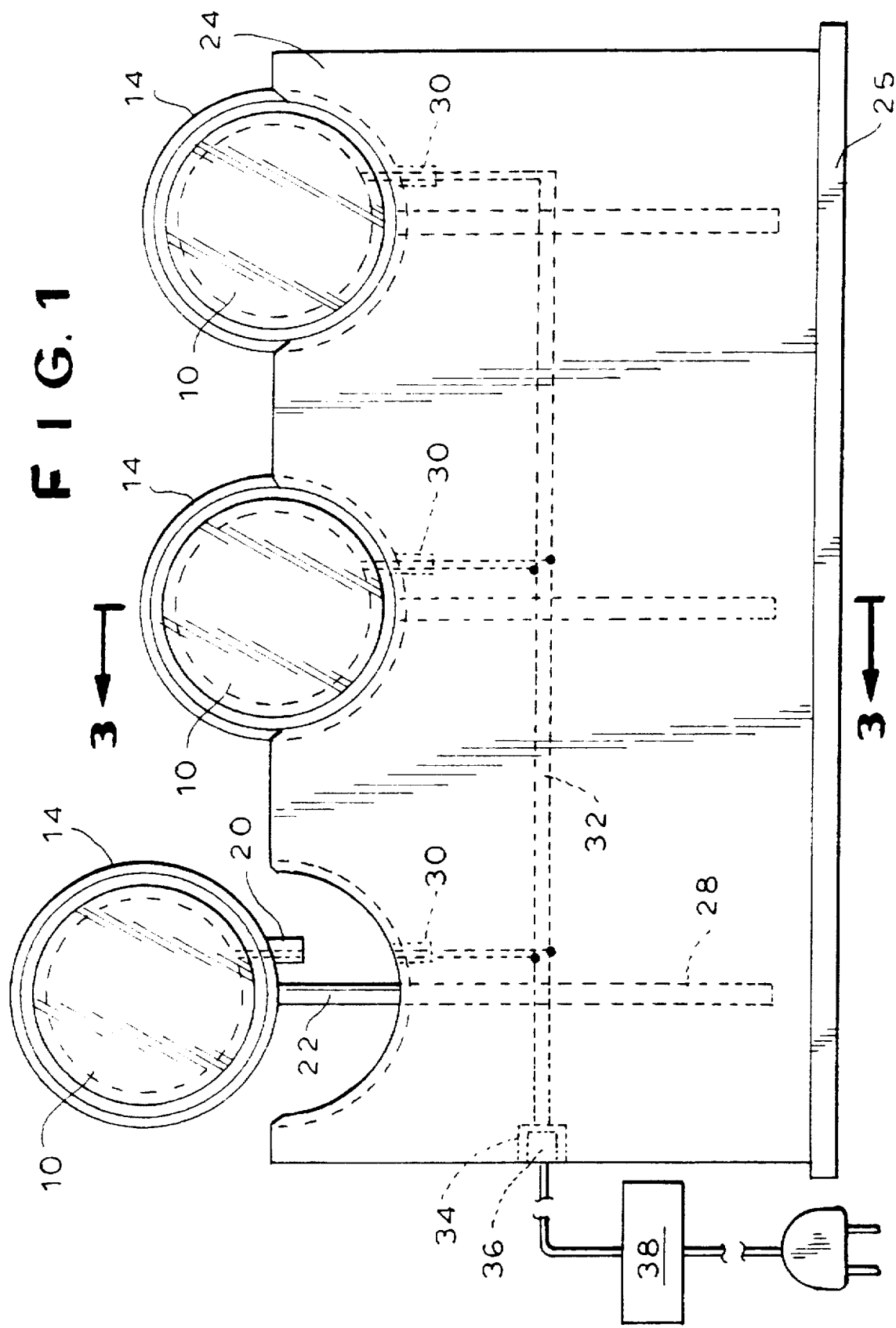
FIG. 1 is a front view of the rack showing three mirror units.

As best seen in FIG. 4, the mirror unit of the present invention includes a round mirror blank 10 with an edge 12. A casing 14 has a side wall 16 with a forward edge which is bent over and sealed to mirror edge 12. Casing 14 is fabricated of heat transmissive material such as metal alloy.

Situtated within the cavity formed between the rear surface of the mirror 10 and the interior of casing 14 is situated an electrically actuated thermofoil heating element 18 which is disk-like in configuration. Heating element 18 is preferrably of the Kapton/FEP type which is made of high strength, high temperature coefficient alloys which resist mechanical stress and are characterized by having a resistance which increases with temperature. Thus, as the temperature increases, the heat output decreases, resulting in a self-regulating heater. There is no need for an external temperature control as the heater will heat to a predetermined temperature level only. Such heaters are commercial available from Minco Products, Inc. of Minneapolis, MN, as well as other sources. Preferrably, the rear surface of the heater is insulated with a clear amber polyimide film 19 with a Teflon adhesive.

Electronically connected to heater 18 is a two prong plug 20 which extends outwardly beyond the surface of casing 14. A handle 22 is provided to facilitate manipulation of the unit. Handle 22 is affixed to the back of case 14.

Figure 2:
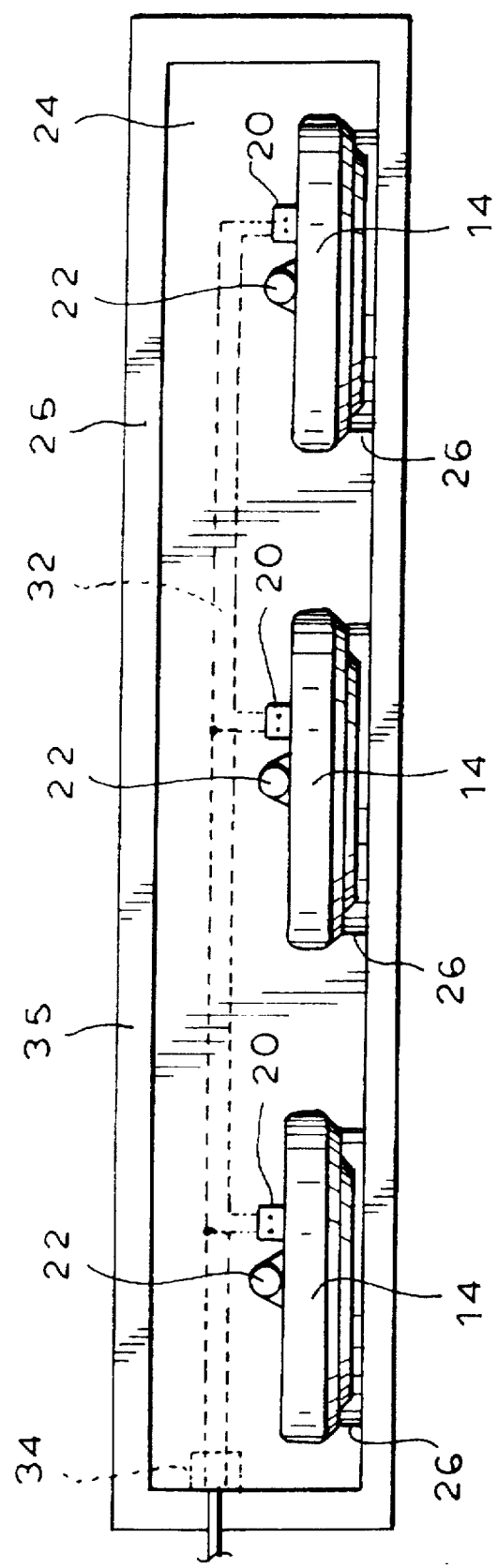
FIG. 2 is a top view of the rack of FIG. 1.

As shown in FIGS. 1, 2 and 3, mirror units of the type described are adapted to nest in a rack 24. Although rack 24 is illustrated as accepting three mirror units, obviously, as many units as is desired can be accommodated. Rack 24 rests on a base 25.

For each mirror unit, the rack includes a semi-circular recess or nest 26 and a cylindrical well 28. The mirror unit is placed in the rack such that the casing wall rests on the top surface of the nest 26 with the handle 22 situated within the adjacent well 28.

Aligned with each nest 26 is a socket 30 adapted to receive the plug 20 of the mirror unit. When plug 20 is situated within socket 30, an electrical connection is completed between a common electrical bus 32 within rack 24 and the heater element of the mirror unit.

Bus 32 is in turn connected to a socket 34 which is situated at the side of the rack. Socket 34 is adapted to accept a plug 36 which is connected to the output of a D.C. transformer 38. Transformer 38 is provided with a plug 40 to be inserted into a standard 120 v A.C. wall socket.

It will now be appreciated that multiple mirror units can be preheated simultaneously on a single rack and used as needed. After use, each mirror unit can be autoclaved. Moreover, the rack itself can be disconnected from the transformer and autoclaved.

The preheated mirror units will heat only to a predetermined temperature level and will maintain that temperature as long as they remain on the rack. In this manner, fogging of the mirror is eliminated. There is no risk of electrical shock or of burning a patient.

While only a single preferred embodiment of the invention is disclosed for purposes of illustration, it is obvious that many variations and modifications could be made thereto. It is intended to cover all of these variations and modifications which fall within the scope of the present invention as defined by the following claims.

I claim:

1. A mirror for dental or medical use comprising a mirror blank having an edge and a rear surface, a casing sealed to said mirror edge, said casing defining a cavity adjacent said rear surface, electrically energizable heat generating means situated within said cavity and means for operably electrically connecting said heat generating means to electrical energizing means, said connecting means comprising first and second interengaging parts, said first part being mounted on and sealed to said casing and said second part being operably electrically connected to an electrical energizing means such that said heat generating means may be energized when said parts are engaged.

2. The mirror of claim 1 wherein said first part comprises a plug.

3. The mirror of claim 1 where said first part comprises a two pronged plug.

4. The mirror of claim 1 wherein said second part comprises a socket.

5. The mirror of claim 1 wherein said electrical energizing means comprises a D.C. transformer, said transformer having an output and wherein said second part is connected to said output.

6. The mirror of claim 1 further comprising rack means for supporting said mirror, said rack means comprising said second part, said first and said second parts interengaging when said mirror is supported by said rack means.

7. The mirror of claim 1 wherein said heat generating means comprises a self-regulating thermofoil heating element.

8. The mirror of claim 7 further comprising an insulating film associated with said element.

9. A mirror energizing system comprising a portable non-fogging mirror unit comprising a casing of a given shape, a mirror sealed to said casing, electrically energizable heat generating means situated within said casing, proximate said mirror and first connecting means mounted on said casing, and a rack, said rack comprising a wall defining a casing receiving recess, said wall having a shape corresponding to said shape of said casing, means for energizing said heat generating means, second connecting means situated in said rack wall so as to engage said first connecting means when said casing is received within said recess, said second connecting means being electrically connected to said energizing means.

10. The system of claim 9 wherein said first connecting means comprises a plug.

11. The system of claim 9 wherein said first connecting means comprises a two pronged plug.

12. The system of claim 9 wherein said second connecting means comprises a socket.

13. The system of claim 9 wherein said heat generating means comprises a self-regulating thermofoil heater element.

14. The system of claim 13 further comprising an insulating film associated with said element.

15. The system of claim 9 wherein said energizing means comprises a D.C. transformer.

16. The system of claim 15 wherein said transformer comprises an output and further comprising means for conditionally connecting said output and said second interengaging means.

17. The system of claim 9 further comprising a second mirror unit and wherein said rack further comprises a second wall defining a second casing receiving recess.

18. The system of claim 17 wherein said second mirror unit comprises first connecting means and said second wall comprises second connecting means.

19. The system of claim 18 further comprising means for conditionally connecting said energizing means and said second connecting means associated with said second wall.

20. The system of claim 9 wherein said rack comprises a support and wherein said wall comprises a part of said support.

21. The system of claim 17 wherein said rack comprises a support and wherein said second wall comprises a part of said support.

* * * * *